United States Patent [19]

Frensch et al.

[11] E Re. 30,740

[45] Reissued Sep. 8, 1981

[54] INSECTICIDAL COMPOSITION FOR ULTRA LOW VOLUME APPLICATION

[75] Inventors: Heinz Frensch, Frankfurt am Main; Konrad Albrecht, Fischbach; Norbert Taubel, Wiesbaden, all of Fed. Rep. of Germany

[73] Assignee: Hoechst Aktiengesellschaft, Frankfurt am Main, Fed. Rep. of Germany

[21] Appl. No.: 3,001

[22] Filed: Jan. 12, 1979

Related U.S. Patent Documents

Reissue of:

[64] Patent No.: 3,952,102
Issued: Apr. 20, 1976
Appl. No.: 536,363
Filed: Dec. 26, 1974

[30] Foreign Application Priority Data

Dec. 28, 1973 [DE] Fed. Rep. of Germany ..... 2364892

[51] Int. Cl.[3] ..... A01N 43/24
[52] U.S. Cl. ..... 424/276
[58] Field of Search ..... 424/276

[56] References Cited

U.S. PATENT DOCUMENTS

| | | | |
|---|---|---|---|
| 2,166,500 | 7/1939 | Lyman | 424/364 X |
| 2,327,152 | 8/1943 | Flaxman | 424/364 X |
| 3,060,085 | 10/1962 | Frensch et al. | 424/276 |
| 3,499,911 | 3/1970 | Zakary | 424/276 X |
| 3,776,857 | 12/1973 | Cindner | 252/308 |

*Primary Examiner*—Leonard Schenkman
*Attorney, Agent, or Firm*—Curtis, Morris & Safford

[57] ABSTRACT

Ultra low volume formulations of endosulfan (6,7,8,9,10,10-hexachloro-1,5,5a,6,9,9a-hexahydro-6,9-methano-2,4,3-benzodioxathiepine-3-oxide), comprising endosulfan, a mixture of a vegetable oil and aromatic hydrocarbons, and an epoxide stabilizer.

3 Claims, No Drawings

INSECTICIDAL COMPOSITION FOR ULTRA LOW VOLUME APPLICATION

Matter enclosed in heavy brackets [ ] appears in the original patent but forms no part of this reissue specification; matter printed in italics indicates the additions made by reissue.

The present invention provides ultra low volume (ULV) formulations of endosulfan (6,7,8,9,10,10-hexachloro-1,5,5a,6,9,9a-hexahydro-6,9-methano-2,4,3-benzodioxathiepine-3-oxide).

Endosulfan is known as insecticide, for example for combating cotton and rice pests and also tsetse flies. It is used in the form of emulsifiable concentrates and wettable powders which, immediately prior to application, are diluted with water and then applied in the form of the spray liquors so obtained by means of spraying apparatus. Generally, from 400 to 6001 of spray liquor per ha are employed. However, this requires large amounts of water which, especially in the tropics, often are not available. Furthermore, at elevated temperature, above all in the case of application by plane, the water content of the spray mist quickly evaporates and the active substance is frequently driven off thus resulting in uneven coverage of the treated area. It was therefore desirable to develop an endosulfan formulation that is essentially free from water. The present invention provides such a formulation, which is in the form of an ultra low volume (ULV) concentrate.

ULV application techniques are already known. In these processes liquid active substances or solutions of active substances in application amounts of from 1 to 5 liters/ha are spread by means of special nozzles. In order to attain a good and homogeneous spreading at such small amounts, the liquids have to be applied in very small droplets of from 75 to 120 microns in diameter, that is, in a far finer distribution than in the conventional spraying of emulsifiable concentrates or wettable powders. ULV formulations therefore have to contain high-boiling solvents in order to prevent quick evaporation and drift-off of the active substance and to prevent crystallization or agglomeration already in the atomizer nozzle. The flash point (closed) of these solvents should therefore be above 55° C. On the other hand, the formulation should not be too viscous, in order to ensure a good and homogeneous atomization of the composition. Although it is possible to spread products having a viscosity of up to 49 centipoises (cp), a more uniform distribution of the droplets is achieved using formulations the viscosity of which is below 20 cP. For the preparation of ULV formulations of solid substance solvents are therefore required which possesses solubility, low voilatility, low viscosity and, above all, a good plant compatibility.

However, the usual paraffinic hydrocarbons and vegetable oils which answer these requirements are unsuitable because of the low solubility (5 to 8%) of endosulfan in these solvents. On the other hand the aromatic solvents generally used in emulsifiable concentrates and which are relatively well tolerated by plants, such as xylene, methylethylketone or cyclohexanone have too high volatility. Finally high-boiling aromatic hydrocarbon fractions and high-boiling ketones such as isophorone are more or less phytotoxic; the toxicity degree rising with increasing boiling point. Furthermore, when testing solutions containing such high-boiling aromatic solvents of for instance, N-methyl-pyrrolidone, and an endosulfan content of about 25 weight %, it turned out that the active substance separated rapidly in the form of coarse crystals from the atomized droplets, thus reducing the insecticidal effect. It is therefore apparent that usual technical solvents commonly used in the preparations of the pesticide formulations do not produce useful ULV formulations of endosulfan.

It has now been found that these drawbacks can be overcome and a stable, technically applicable ultra low volume (ULV) formulation of endosulfan is obtained by combining a. 15 to 35 weight % of endosulfan;

b. 60 to 84.5 weight % of a solvent mixture of from 1.5 to 2.5 parts by weight of a vegetable oil, and from 0.5 to 1.5 parts by weight of aromatic hydrocarbons having boiling ranges of from 170° to 250° C.; and c. 0.5 to 6 weight % of an epoxide.

Suitable vegetable oils ar for example rapeseed, cottonseed, peanut, sunflower or safflower oil.

Preferred aromatic hydrocarbons are alkyl benzenes of 9 to 11 carbon atoms, such as the various trimethylbenzenes, methyl-ethyl benzenes, dimethyl-ethyl benzenes, diethyl benzenes, tetramethyl benzenes, trimethyl-ethyl benzenes, methyl-diethyl benzenes, pentamethyl benzene or mixtures thereof; furthermore 1- and 2-methyl naphtalene. By way of example the following technical products which essentially consist of the above compounds are mentioned. (R)"Shellsol AB" (Shell), boiling range 187°-213° C., (R)"Solvesso 150" (Exxon), boiling range 183°-207° C., (K) "Aromasol H" (ICI), boiling range 168°-200° C.

Suitable epoxides are for example epichlorohydrin, epoxypropane, styrene oxide, phenylepoxypropane or epoxides of unsaturated vegetable oils such as linseed oil epoxide or soy bean oil epoxide. Preferably, epichlorohdrin is used in an amount of from 0.5 to 2 weight %.

Surprisingly, despite the poor solubility of endosulfan in vegetable oils and despite the still existing volatility of the solvents added, no endosulfan crystallizes from the fine droplets of the layers spread in ULV application even after 7 to 10 days. Endosulfan in the formulation according to the invention has therefore a far higher efficiency and a longer activity period, as compared with the commercial emulsifiable concentrate of endosulfan, so that the same effect is otained using less active substance, and the application intervals may be considerably extended.

The products furthermore have a good resistance against rain, good adhesiveness and plant compatibility. The formulations have flash points from 50° to 72° C. according to the Pensky-Martens method and a viscosity of from 10 to 15 centipoises at 20° C. Thus, they meet the usual requirements for ULV products. The vegetable oils have no influence on the chemical stability of endosulfan. Even under tropical conditions, the products are stable over more than two years.

The following examples illustrate the invention. The endosulfan active substance is advantageously dissolved as far as possible in the aromatic solvent, subsequently the vegetable oil and the stabilizer are added, and agitation is continued until the active substance is completely dissolved.

Composition of some endosulfan ULV formulations:

EXAMPLE 1

25 weight % of endosulfan 1 weight % of epichlorohydrin 29 weight % of (R)Shellsol AB*
45 weight % of rapeseed oil

*Shellsol AB has the following physical characteristics: content of aromates 95.5%; boiling range 187°-213° C.; flash point (closed) 66° C.

EXAMPLE 2

25 weight % of endosulfan
1 weight % of epichlorohydrine
37 weight % of (R)Solvesso 150*
37 weight % of cottonseed oil

*Solvesso 150 has the following physical characteristics: content of aromates 97%; boiling range 183°-207° C.; flash point (closed) 66° C.; density 0.895 (15° C.).

EXAMPLE 3

35 weight % of endosulfan
1.5 weight % of epoxylated soybean oil
32 weight % of (R)Shellsol AB
31.5 weight % of rapeseed oil.

EXAMPLE 4

In comparison to a commercial emulsifiable concentrate containing 35% of endosulfan (EC) (Example 3), the ULV formulation of Example 1 was tested as to effect and activity period.

In a spray tower, plants of horse beans (Vicia faba) were sprayed according to the ULV process with the endosulfan 25 ULV product according to Example 1, and, for comparison, with a commercial endosulfan 35 EC emulsion. The plants were then kept in a moisture chamber under constant conditions (temperature 20° C., relatice humidity 50–60%). The amount of product applied corresonded to a dose of 300 g of active substance/ha.

Parts of these bean plants were cut off in intervals of 1, 2, 3, 5 and 7 days and were put with the lower ends into little glass tubes filled with water. These were then placed into a paperboard cup which was covered with wire fabric, and 10 larvae of Prodenia (L 3) each (5 parallel tests) were placed onto the plant cuttings.

Examination was carried out after 3, 24, 48 and 72 hours. With respect to mortality, the composition of Example 1 was clearly superior to the comparative product.

| Product | Conc. of AS (g/ha) | 1 day hours | | | | 2 days hours | | | 3 days hours | | | 7 days hours | | |
|---|---|---|---|---|---|---|---|---|---|---|---|---|---|---|
| | | 3 | 24 | 48 | 72 | 24 | 48 | 72 | 24 | 48 | 72 | 24 | 48 | 72 |
| Endosulfan 25 ULV | 300 | 14* | 42 | 42 | 47 | 36 | 30 | 30 | 23 | 27 | 28 | 17 | 20 | 21 |
| 35 EC | 300 | 10 | 38 | 38 | 38 | not tested | | | 12 | 13 | 13 | 0 | 0 | 1 |

*% mortality

What is claimed is:

1. An insecticidal composition for ultra low volume application, which comprises
   a. from 15 to 35 weight % of 6,7,8,9,10,10-hexachloro-1,5,5a,6,9,9a-hexahydro-6,9-methano-2,4,3-benzodioxathiepine-3-oxide,
   b. from 60 to 84.5 weight % of a solvent mixture of 1.5 to 2.5 parts by weight of a vegetable oil consisting of rapeseed, cottonseed, peanut, sunflower, or safflower oil, and from 0.5 to 1.5 parts by weight of an aromatic hydrocarbon having a boiling range of from 170° to 250° C. consisting of one or more alkyl benzenes having 9 to 11 carbon atoms; or 1-or 2-methyl naphthalene; and
   c. from 0.5 to 6 weight % of an epoxide selected from the group consisting of epichlorohydrin, epoxypropane, styrene oxide, phenylepoxy propane, and an expoxide of an unsaturated vegetable oil.

2. An insecticidal composition as claimed in claim 1, wherein the epoxide is epichlorohydrin.

3. An insecticidal composition as claimed in claim 1, wherein epichlorohydrin is 0.5 to 2% by weight of said composition.

* * * * *